United States Patent [19]

Krafft

[11] Patent Number: 5,681,976
[45] Date of Patent: Oct. 28, 1997

[54] PREPARATION OF BIS(ACETONITRILE) PALLADIUM DICHLORIDE

[75] Inventor: Terry E. Krafft, Longmont, Colo.

[73] Assignee: Boulder Scientific Company, Mead, Colo.

[21] Appl. No.: 512,623

[22] Filed: Aug. 8, 1995

[51] Int. Cl.$^6$ .................................................. C07F 15/00
[52] U.S. Cl. ........................................ 556/137; 423/491
[58] Field of Search ............................ 556/137; 423/491

[56] References Cited

PUBLICATIONS

Greenwood et al, "Chemistry of the Elements", QD 466 G74, 1984 (no month), pp. 1339–1340.
Bailar et al, "Comprehensive Inorganic Chemistry", QP 151.2 C64 1973 (no month), p. 1329.
Bailar et al. "Comprehensive Inorganic Chemistry", 1973, pp. 1304–1312 (no month).
Brauer, "Handbook of Preparative Inorganic Chemistry", vol. 2, 2nd edition, p. 1582 QD 151 B7, 1963 (no month).
Grant & Hackh's, "Chemical Dictionary", Fifth edition, Q5 H3, 1987, pp. 281, 371 (no month).

*Primary Examiner*—Ngoc-Yen Nguyen
*Attorney, Agent, or Firm*—Edward S. Irons

[57] ABSTRACT

A method for the production of tetrachloropalladic acid and bis(acetonitrile) palladium dichloride is described. Palladium metal is reacted with concentrated hydrochloric acid and chlorine to produce the acid which is converted to bis(acetonitrile) palladium dichloride by reaction with acetonitrile.

5 Claims, No Drawings

PREPARATION OF BIS(ACETONITRILE) PALLADIUM DICHLORIDE

TECHNICAL FIELD

This invention relates to the preparation of tetrachloropalladic acid and of bis(acetonitrile) palladium dichloride.

BACKGROUND OF THE INVENTION bis(acetonitrile) palladium dichloride is a commercially important catalyst useful in a broad range of organic reactions. See, e.g., Heck, R. F. "Palladium Reagents in Organic Synthesis" (1985) Academic Press, New York; Tsuji, J. "Organic Synthesis With Palladium Compounds" (1980) Springer-Verlag, New York.

Known methods for producing Bis(acetonitrile) palladium dichloride entail dissolution of the metal in aqua regia, conversion to tetrachloropalladic acid, conversion of the acid to one of several known salts, isolation of the salt and subsequent reaction to produce the desired product as shown by equations 1, 2 and 3:

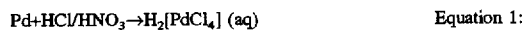
Pd+HCl/HNO$_3$→H$_2$[PdCl$_4$] (aq)   Equation 1:

H$_2$[PdCl$_4$]+MCl→M$_2$[PdCl$_4$] M=K, Na, NH$_4$   Equation 2:

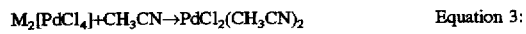
M$_2$[PdCl$_4$]+CH$_3$CN→PdCl$_2$(CH$_3$CN)$_2$   Equation 3:

See Kauffman, G. B., et al., *Inorg. Synth.* (1966) 8:234.

Alternatively, bis(acetonitrile) palladium dichloride can be made by reaction of palladium dichloride with acetonitrile as shown by equation 4:

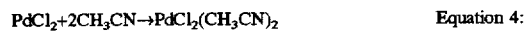
PdCl$_2$+2CH$_3$CN→PdCl$_2$(CH$_3$CN)$_2$   Equation 4:

See, Hartley, F. R., et al., *Inorgan. Chem.* (1979) 18:1394; Wayland, B. B., et al., *Inorgan. Chem.* (1969) 8:971; Ketley, German Patent No. 1,810,122 (03 Jul. 1969); Anderson, G. K., et al., *Inorgan. Synth.* (1990) 28:60; Kharasch, M. S., et al., *J. Am. Chem. Soc.* (1938) 60:882.

SUMMARY OF THE INVENTION

Pursuant to this invention, tetrachloropalladic acid is formed by dissolving palladium in a mixture of concentrated hydrochloric acid and chlorine and expelling the excess HCl and Cl$_2$ by distillation. This synthesis is illustrated by equations 5 and 6:

Equation 5:
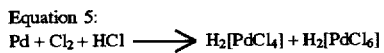
Pd + Cl$_2$ + HCl ⟶ H$_2$[PdCl$_4$] + H$_2$[PdCl$_6$]

Equation 6:
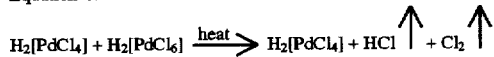
H$_2$[PdCl$_4$] + H$_2$[PdCl$_6$] $\xrightarrow{heat}$ H$_2$[PdCl$_4$] + HCl↑ + Cl$_2$↑

Pursuant to another aspect of the invention, direct addition of acetonitrile to an aqueous solution of tetrachloropalladic acid yields bis(acetonitrile) palladium dichloride in good yield which may exceed 90%. This reaction is illustrated by equation 7:

H$_2$[PdCl$_4$] (aq)+CH$_3$CN )→PdCl$_2$(CH$_3$CN)$_2$(>90% overall)

Equation 7:

The three reactions shown by equations 5, 6 and 7 are appropriately run in a single vessel without isolation of any intermediates.

DETAILED DESCRIPTION OF THE INVENTION

This invention provides novel methods for the preparation of tetrachloropalladic acid and of bis(acetonitrile) palladium dichloride. In the preferred practice of the invention, a reaction vessel fitted with a mechanical stirrer and a subsurface gas delivery tube is charged with palladium sponge. At least 1.0 molar, preferably 6.0 to 12.0 molar hydrochloric acid is added to the reaction vessel. Chlorine gas is added to the reaction vessel contents at a temperature of 0° C. to 120° C. with stirring. Room temperature is appropriate. Higher temperatures may be employed if the reaction vessel is pressurized. Formation of a deep red-orange solution indicates the formation of tetrachloropalladic acid. The passage of chlorine gas through the reaction mixture is continued for a time period appropriate to produce a desired quantity of such acid. In general, the chlorine gas passes through the reaction mixture for a time period of five to ten hours.

The product of this reaction is concentrated and excess hydrochloric acid and chlorine are expelled from it by distillation to provide an aqueous solution at least 0.1 molar, preferably 4.0 to 6.0 molar tetrachloropalladic acid.

The concentrated acid solution, after filtration, is diluted with water to a molarity of at least 0.1 molar, preferably a molarity of 0.2 to 0.6.

Acetonitrile is added with stirring to the diluted tetrachloropalladic acid solution in an amount stoichiometrically required to produce bis(acetonitrile) palladium dichloride pursuant to equation 7. The acetonitrile may be added in an amount more or less than the stoichiometric amount if it is desired to do so. The yield of this acetonitrile palladium dichloride is a function of the amount of acetonitrile added to the tetrachloropalladic acid solution. The reaction is appropriately stirred at room temperature for a reasonable time, e.g., one hour, and thereafter with ice cooling for an additional time, e.g., one hour. This reaction produces the desired bright orange bis(acetonitrile) palladium dichloride product. The product is collected, washed sequentially with water and acetonitrile and dried.

EXEMPLIFICATION OF THE INVENTION

A 3 liter 3-neck flask fitted with a mechanical stirrer and subsurface gas delivery tube was charged with palladium sponge (497.3 g). Concentrated hydrochloric acid (3,188 g) was added to the flask. Chlorine gas was slowly bubbled through the solution while stirring at room temperature for a total of eight hours. The deep red-orange solution was transferred to a 5 liter 3-neck flask fitted with a mechanical stirrer, claissen adapter, still head, condenser and weighed receiver. The solution was concentrated to a total weight of 1,717 g by distillation.

The concentrated solution was filtered through a Buchner funnel and divided equally between two 12 liter flasks. The solution in each flask was diluted with water to a total weight of 6,389 g. Each flask was fitted with a mechanical stirrer and while stirring at room temperature, acetonitrile (1,200 mL 99.9%) was added all at once. Each flask was stirred one hour at room temperature and then one hour with ice water cooling.

The bright orange product was collected in a large Buchner funnel and washed with 2×1 liter of water and then with 1 liter of CH$_3$CN. The product was air dried to a constant weight. A total of 1,109 g (91.5% yield) of crystalline product was obtained. The material was identified by comparison of the IR spectrum with an authentic sample.

I claim:

1. A method for producing bis(acetonitrile) palladium dichloride which comprises conducting reactions 1, 2 and 3 sequentially in a single vessel without isolation of any intermediate product wherein said reactions 1, 2 and 3 are:

Reaction 1:
$$Pd + Cl_2 + HCl \longrightarrow H_2[PdCl_4] + H_2[PdCl_6]$$

Reaction 2:
$$H_2[PdCl_4] + H_2[PdCl_6] \xrightarrow{heat} H_2[PdCl_4] + HCl\uparrow + Cl_2\uparrow$$

Reaction 3:
$$H_2[PdCl_4] + CH_3CN \longrightarrow PdCl_2(CH_3CN)_2$$

wherein a reaction product containing bis(acetonitrile) palladium dichloride is produced in said single vessel.

2. The claim 1 method in which said bis(acetonitrile) palladium dichloride produced in said single vessel is isolated.

3. A method for producing bis(acetonitrile) palladium dichloride which comprises
  (i) providing a single reaction vessel,
  (ii) reacting palladium with chlorine and aqueous hydrochloric acid in said reaction vessel to produce a first reaction mixture comprising $H_2[PdCl_4]$ and $H_2[PdCl_6]$,
  (iii) heating said first reaction mixture to evolve chlorine and hydrogen chloride and produce a second reaction mixture containing $H_2[PdCl_4]$ and
  (iv) adding $CH_3CN_2$ to said second reaction mixture for reaction with said $H_2[PdCl_4]$ to produce a third reaction mixture containing bis(acetonitrile) palladium dichloride.

4. The claim 3 method further comprising isolating said bis(acetonitrile) palladium dichloride from said third reaction product.

5. The claim 3 method wherein said acetonitrile is added to said second reaction product in an amount stoichiometrically required to produce bis(acetonitrile) palladium dichloride from the $H_2[PdCl_4]$ present in said second reaction mixture.

* * * * *